US010786341B2

(12) United States Patent
Chen et al.

(10) Patent No.: US 10,786,341 B2
(45) Date of Patent: Sep. 29, 2020

(54) MICRO-CHANNEL IMAGING SYSTEM FOR LIVING ORGANISM

(71) Applicant: NATIONAL CHENG KUNG UNIVERSITY, Tainan (TW)

(72) Inventors: Chia-Yuan Chen, Tainan (TW); Karthick Mani, Tainan (TW); Pin-Yi Huang, Tainan (TW); Zong-Yi Lu, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 435 days.

(21) Appl. No.: 15/829,923

(22) Filed: Dec. 3, 2017

(65) Prior Publication Data

US 2019/0117361 A1    Apr. 25, 2019

(30) Foreign Application Priority Data

Oct. 25, 2017    (TW) .............................. 106136782 A (51) Int. Cl.
*A61D 3/00*         (2006.01)
*A61B 5/00*         (2006.01)

(52) U.S. Cl.
CPC .............. *A61D 3/00* (2013.01); *A61B 5/0059* (2013.01); *A61B 2503/40* (2013.01)

(58) Field of Classification Search
CPC ...... A61B 2503/40; A61B 5/0059; A61D 3/00
See application file for complete search history.

(56) References Cited

U.S. PATENT DOCUMENTS

| 2015/0097317 | A1* | 4/2015 | Chen ..................... B29C 39/026 |
| | | | 264/429 |
| 2016/0327545 | A1* | 11/2016 | Shi ...................... G01N 33/5088 |
| 2017/0086430 | A1* | 3/2017 | Wills ..................... A23K 50/60 |
| 2017/0293130 | A1* | 10/2017 | Huang ............... G02B 21/0088 |

OTHER PUBLICATIONS

Mani et al., "Orientation control of zebrafish embryos using artificial cilia in a 3D flow-through nnicrochannel," 10th IEEE International Conference on Nano/Micro Engineered and Molecular Systems, Xi'an, 2015, pp. 15-19. (Year: 2015).*
Karthick Mani, Tsung-Chun Chang Chien, Bivas Panigrahi and Chia-Yuan Chen, Manipulation of zebrafish's orientation using artificial cilia in a microchannel with actively adaptive wall design Scientific Reports vol. 6, No. 36385(2016).

* cited by examiner

*Primary Examiner* — Amelie R Davis
(74) *Attorney, Agent, or Firm* — Soroker Agmon Nordman (57) ABSTRACT

An imaging system for a living organism is described and has a receiving device used to receive the living organism and formed with at least two receiving grooves, at least one micro-channel connected to the receiving grooves, and a plurality of magnetic cilia disposed on a surface of the micro-channel; a magnetic field providing device neighboring a first side of the receiving device to control an action of the magnetic cilia; a driving device neighboring a second side of the receiving device to drive a movement of the living organism and control a moving direction thereof; a liquid providing device in communication with the receiving device to provide liquid; and an image capturing device neighboring a third side of the receiving device to capture an image of the living organism.

6 Claims, 10 Drawing Sheets

MICRO-CHANNEL IMAGING SYSTEM FOR LIVING ORGANISM

CROSS REFERENCE TO RELATED APPLICATION

This application claims priority to Taiwan Patent Application No. 106136782, filed on Oct. 25, 2017, which is incorporated herein by reference in its entirety.

FIELD OF THE DISCLOSURE

The present disclosure relates to an imaging system, and more particularly to an imaging system for a living organism.

BACKGROUND OF THE DISCLOSURE

In recent years, zebrafish have become an important reference for the study of vertebrates in the biomedical community. This is because the zebrafish have characteristics of small size, fast growth, good optical transparency, and high similarities with human genes, etc.

However, during observation of the zebrafish, it is necessary to manually move the zebrafish from a cultivation area onto an observation platform for observation. However, this manual clamping method often causes damage to the zebrafish, so it is easy to misjudge observation results and further affect experimental results.

As a result, it is necessary to provide an imaging system for a living organism to solve problems existing in conventional technologies, as described above.

SUMMARY OF THE DISCLOSURE

An object of the present disclosure is to provide an imaging system for a living organism, which can be used to observe quantity the blood flow in the living organism (such as a zebrafish or a zebrafish sperm) located in a receiving device, and the living organism can be driven by a driving device so as to move to an observing position. Therefore, there is no need to move the living organism by a manual clamping method.

Another object of the present disclosure is to provide an imaging system for a living organism, which can control at least one flipping angle of the living organism in a stepwise manner by a plurality of magnetic cilia, so as to observe the living organism using a plurality of observing angles.

A further object of the present disclosure is to provide an imaging system for a living organism, which can activate frozen zebrafish sperm by an action of a plurality of magnetic cilia.

To achieve the above objects, the present disclosure provides an imaging system, suitable for a living organism, including:
  a receiving device configured to receive the living organism, the receiving device including:
    at least two receiving grooves;
    at least one microchannel in communication with the receiving grooves; and
    a plurality of magnetic cilia disposed on a surface of the microchannel;
  a magnetic field control device neighboring a first side of the receiving device and configured to control an action of the magnetic cilia;
  a driving device neighboring a second side of the receiving device and configured to drive a movement of the living organism and control a moving direction thereof;
  a liquid buffer circulating device in communication with the receiving device and configured to provide liquid; and
  an image acquisition device neighboring a third side of the receiving device and configured to acquire an image of the living organism.

In some embodiments of the present disclosure, the living organism is one of a zebrafish and a zebrafish sperm.

In some embodiments of the present disclosure, the imaging system further includes a moving frame, wherein the receiving device is disposed on the moving frame.

In some embodiments of the present disclosure, the imaging system further includes a flow control device electrically connected to the liquid buffer circulating device and configured to control flow of the liquid.

In some embodiments of the present disclosure, the imaging system further includes a controlling device electrically connected to one of the magnetic field control device, the driving device, and the image acquisition device.

In some embodiments of the present disclosure, the controlling device further includes a graphical user interface configured to control one of the magnetic field control device, the driving device, and the image acquisition device by inputting an instruction to the graphical user interface.

In some embodiments of the present disclosure, the driving device includes at least one of a light driving device and a hydrodynamic driving device.

In some embodiments of the present disclosure, the light driving device projects a light pattern into the receiving device, and the light pattern includes a plurality of linear bright fringes and a plurality of linear dark fringes, both of which are alternately arranged in sequence.

In some embodiments of the present disclosure, the light pattern is a dynamic pattern, and the linear bright fringes and the linear dark fringes move along a proceeding direction.

In some embodiments of the present disclosure, each of the magnetic cilia has an axial direction vertical to the surface of the microchannel, and the action of the magnetic cilia includes one action selected from:
  a tilting action, wherein each of the magnetic cilia has a tilting angle with respect to the axial direction; and
  a rotating action, wherein each of the magnetic cilia has the tilting angle with respect to the axial direction, and the magnetic cilia rotate around a rotation axis defined by the axial direction.

DETAILED DESCRIPTION OF THE PREFERRED EMBODIMENTS

The structure and the technical means adopted by the present disclosure to achieve the above and other objects can be best understood by referring to the following detailed description of the preferred embodiments and the accompanying drawings. Furthermore, directional terms described by the present disclosure, such as upper, lower, front, back, left, right, inner, outer, side, longitudinal/vertical, transverse/horizontal, etc., are only directions by referring to the accompanying drawings, and thus the used directional terms are used to describe and understand the present disclosure, but the present disclosure is not limited thereto.

Figure 1A:
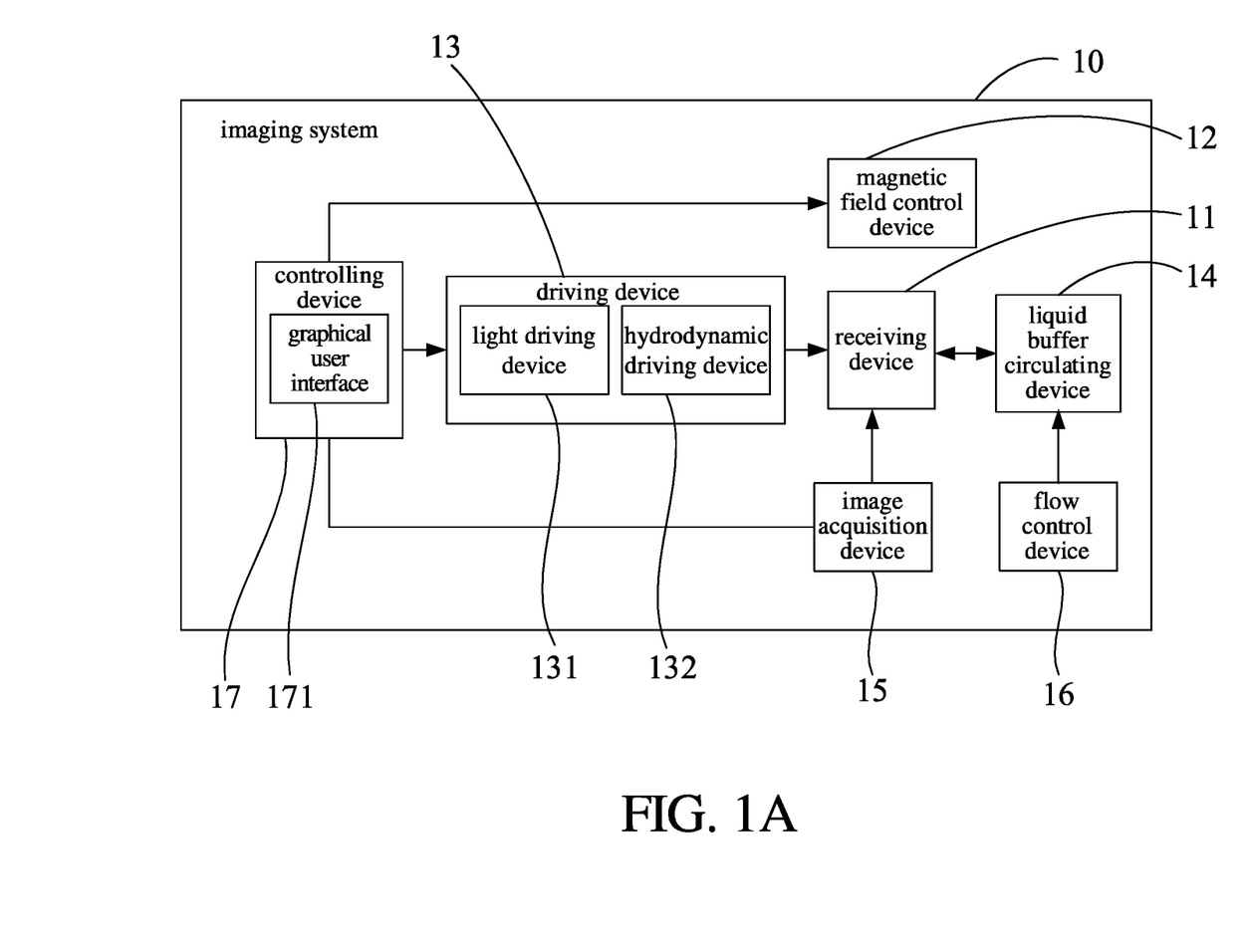
FIG. 1A is a block schematic diagram illustrating an imaging system suitable for a living organism according to some embodiments of the present disclosure.
Figure 1B:
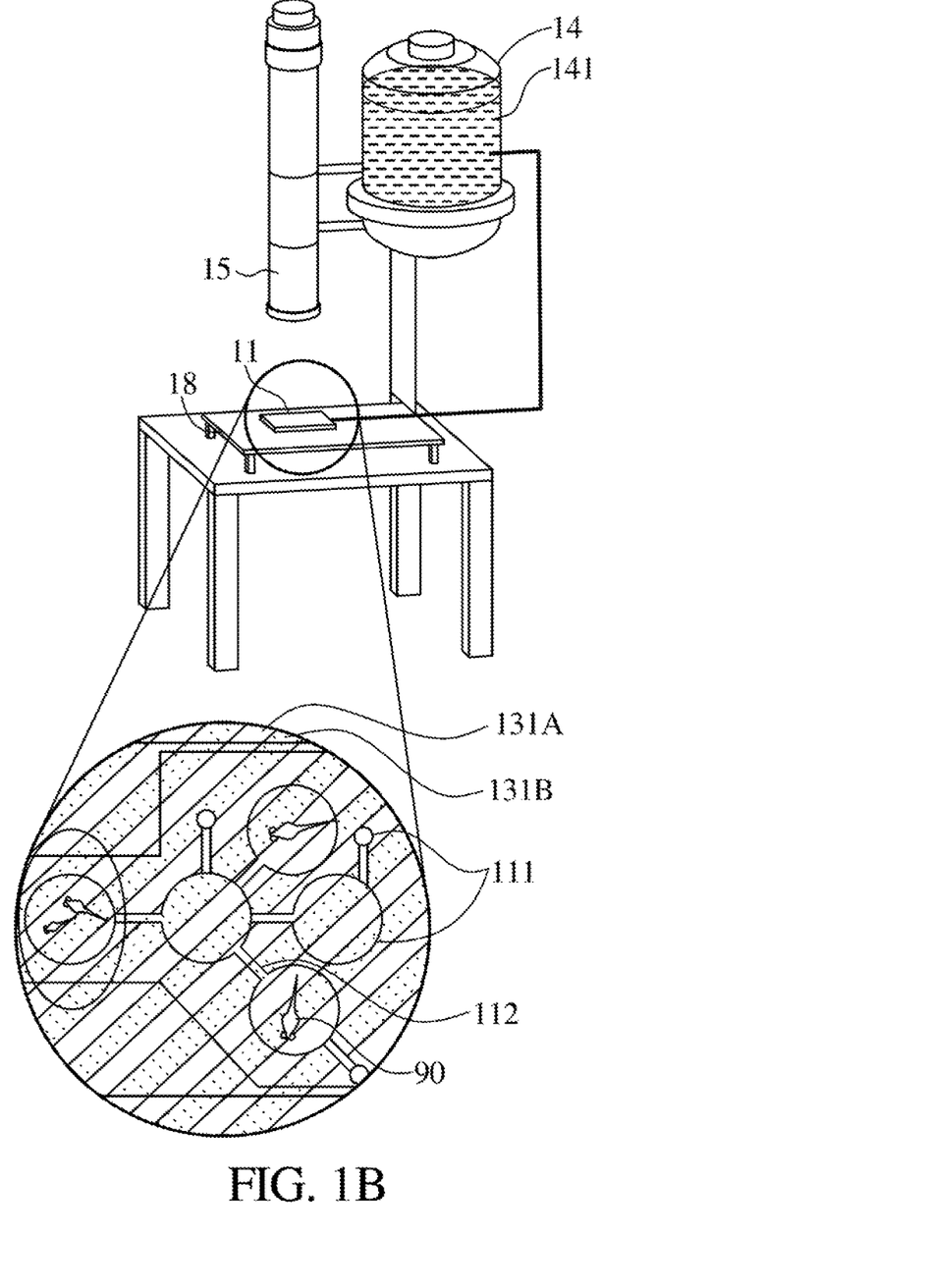
FIG. 1B is a three dimensional schematic diagram illustrating an imaging system suitable for a living organism according to some embodiments of the present disclosure.
Figure 2A:
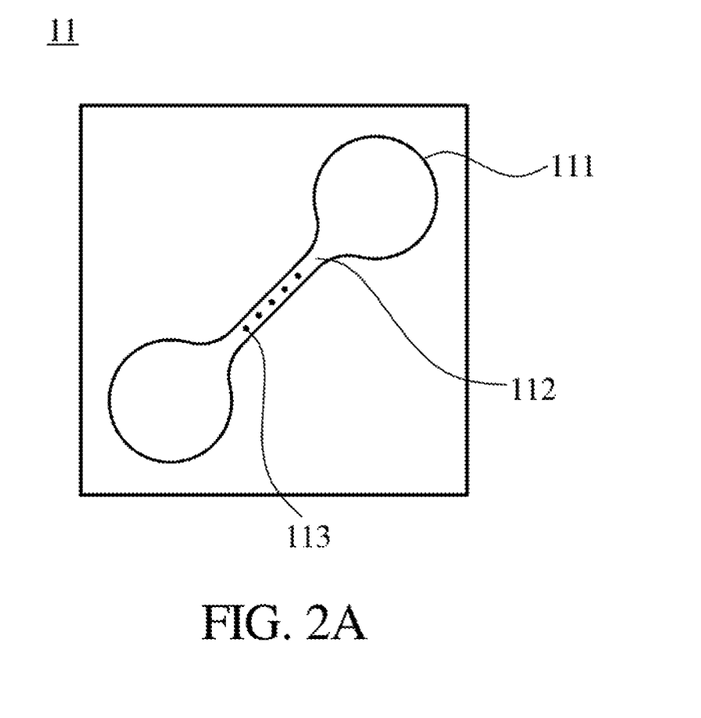
FIG. 2A is a schematic top view illustrating a receiving device (with magnetic cilia embedded) according to another embodiment of the present disclosure.
Figure 2B:
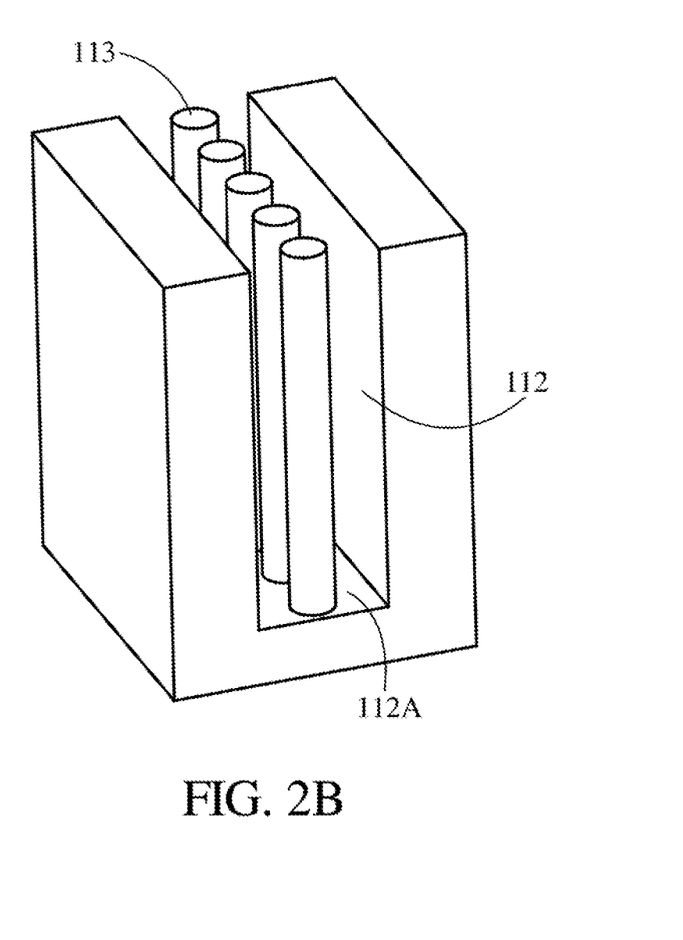
FIG. 2B is a three dimensional schematic diagram illustrating a microchannel and a plurality of magnetic cilia according to another embodiment of the present disclosure.

Referring to FIG. 1A to FIG. 2A, FIG. 1A is a block schematic diagram illustrating an imaging system 10 according to some embodiments of the present disclosure, FIG. 1B is a three dimensional schematic diagram illustrating an imaging system 10 according to some embodiments of the present disclosure, FIG. 2A is a schematic top view illustrating a receiving device 11 (with magnetic cilia embedded) according to another embodiment of the present disclosure, and FIG. 2B is a three dimensional schematic diagram illustrating a microchannel 112 and a plurality of magnetic cilia 113 according to another embodiment of the present disclosure. In some embodiments of the present disclosure, the imaging system 10 includes a receiving device 11, a magnetic field control device 12, a driving device 13, a liquid buffer circulating device 14, and an image acquisition device 15. In some embodiments, the living organism 90 can be a living animal with a length less than 10 cm, e.g., the length being 1 cm, 2 cm, 5 cm, 8 cm, etc. In some embodiments, the living organism 90 can be a small or micro vertebrate or sperm thereof, and particularly a small fish or sperm thereof with a length less than 5 mm or less than 10 mm, e.g., one of a zebrafish and a zebrafish sperm. In some examples, the living organism 90 can be a living aquatic animal. In some embodiments, the receiving device 11 is used to receive the living organism 90. In some examples, the receiving device 11 can be also used as a cultivating container of the living organism 90. For example, at least one frozen zebrafish sperm can be placed in the receiving device 11 to perform an activating treatment. Then, at least one zebrafish ova is placed in the receiving device 11 such that the zebrafish sperm together with the zebrafish ova form at least one fertilized egg and develop into at least one zebrafish to be observed. In some embodiments, the receiving device 11 can be made of a transparent material, so as to observe an image of the living organism 90.

The receiving device 11 can include at least two receiving grooves 111, at least one microchannel 112, and a plurality of magnetic cilia 113. In one embodiment, the receiving grooves 111 can have different sizes (as shown in FIG. 1B), and the number of the receiving grooves 111 can be greater than two (as shown in FIG. 1B). In another embodiment, the microchannel 112 of the receiving device 11 is in communication with the receiving grooves 111 so as to enable the living organism to move to each of the receiving grooves 111 by the microchannel 112. In some embodiments, the magnetic cilia 113 are disposed on a surface 112A of the microchannel 112. For example, the surface 112A is a bottom surface of the microchannel 112. In a specific example, the magnetic cilia 113 can be disposed along the microchannel 112 (as shown in FIG. 2B) or can also be arranged in a matrix manner in the microchannel 112.

In some embodiments, the receiving grooves 111 can be used as embryo storage grooves of the living organisms 90. For example, at least one of the grooves can be defined as the embryo culture groove or the embryo storage groove of the living organisms 90. Then, after incubation of living organisms 90 is completed, an image capturing can be performed by the image acquisition device 15, or the living organisms 90 can be driven by the driving device 13.

It is noted that materials and manufacturing methods of the microchannel 112 and the magnetic cilia 113 can be made according to or with reference to the approved Taiwan Patent (No. 1515039; manufacturing method of magnetic cilia). In some embodiments, the receiving grooves 111 can be round grooves with a diameter ranging from 1 to 2 mm. In some embodiments, the microchannel 112 has a length ranging from 4 to 8 mm and a width ranging from 0.1 to 0.3 mm. In a further embodiment, each of the magnetic cilia 113 has such as a cylindrical shape, where each of the magnetic cilia 113 has a length such as ranging from 0.3 to 0.5 mm and a diagram ranging from 0.01 to 0.1 mm. In another embodiment, a distance between neighboring magnetic cilia 113 ranges such as 0.1 to 0.3 mm.

Figure 2C:
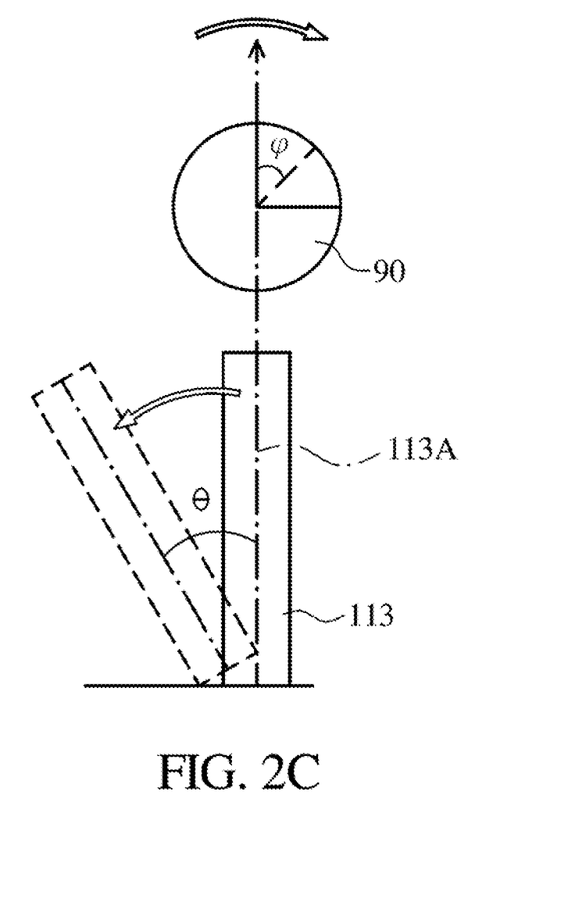
FIG. 2C is a cross-sectional diagram illustrating a tilting angle of the magnetic cilia and a flipping angle of the living organism.
Figure 2D:
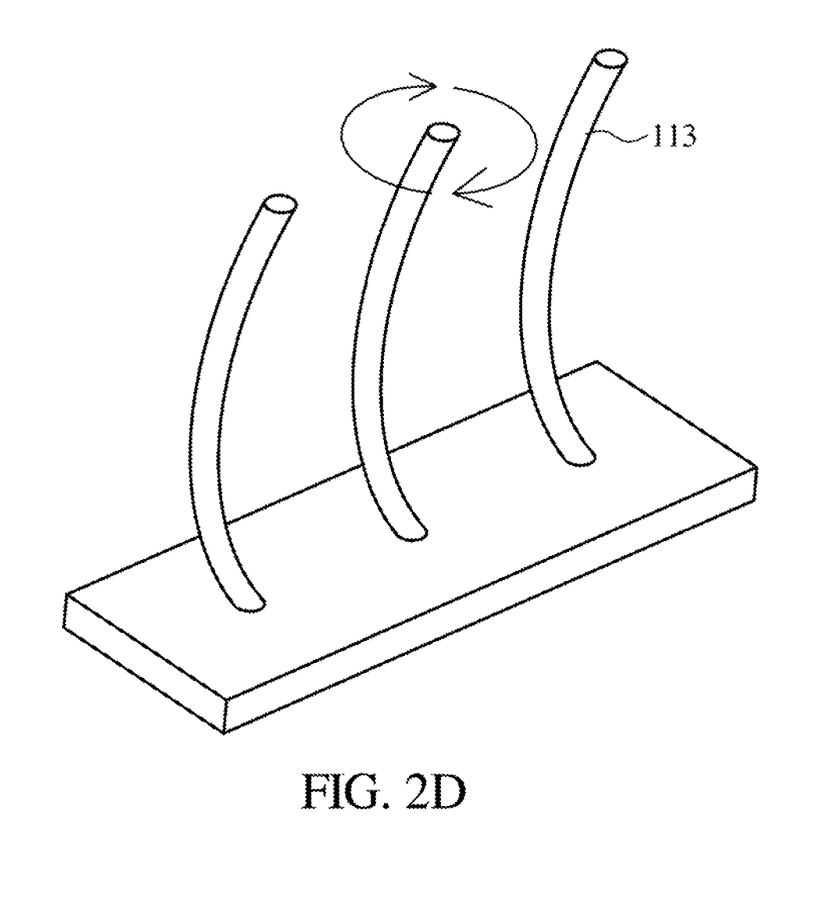
FIG. 2D is a three dimensional schematic diagram illustrating the magnetic cilia with a rotating action.

The magnetic field control device 12 of the imaging system 10 neighbors a first side of the receiving device 11 and is used to control an action of the magnetic cilia 113. In some embodiments, the magnetic field control device 12 can control the action of the magnetic cilia 113 by providing a magnetic field. In a specific example, each of the magnetic cilia 113 has an axial direction 113A vertical to the surface 112A of the microchannel 112, and the action of the magnetic cilia 113 includes one of actions selected from: a tilting action, wherein each of the magnetic cilia 113 has a tilting angle θ (as shown in FIG. 2C) with respect to the axial direction 113A; and a rotating action, wherein each of the magnetic cilia 113 has the tilting angle θ (as shown in FIG. 2C) with respect to the axial direction 113A, and the magnetic cilia 113 rotate around a rotation axis defined by the axial direction 113A (as shown in FIG. 2D). In some embodiments, the living organism (such as a zebrafish) can be affected to produce a flipping angle φ (as shown in FIG. 2C) by the tilting action, so as to acquire images of the living organism at different angles by the image acquisition device. Detailed experimental results will be described below. In some embodiments, an axial rotating control of the living organism is in a stepwise (such as about 2 degrees every step) and highly accurate manner. In another embodiment, the rotating action can promote activation of the frozen zebrafish sperm, and detailed experimental results will be described below.

A driving device 13 of the imaging system 10 neighbors a second side of the receiving device 11 and is used to drive a movement of the living organism 90 and control a moving direction thereof. In one embodiment, the living organism 90 moves to an area (e.g., the receiving groove 111 or the microchannel 112) using the driving device 13 by means of non-forcibly moving. In a specific example, the driving device 13 includes at least one of a light driving device 131 and a hydrodynamic driving device 132. In an example, the light driving device 131 projects a light pattern into the receiving device 11, and the light pattern includes a plurality of linear bright fringes 131A and a plurality of linear dark fringes 131B, both of which are alternately arranged in sequence. More specifically, the light pattern can be a dynamic pattern, and the linear bright fringes 131A and the linear dark fringes 131B move along a proceeding direction. Detailed experimental results will be described below. In another example, the hydrodynamic driving device 132 mainly changes a flow field of liquid 141 in the receiving device 11 so as to drive a moving direction of the living organism 90. For example, the hydrodynamic driving device 132 can produce a specific flow field by the liquid buffer circulating device 14 which provides a specific flow (such as 4 to 6 cm$^3$/min) into the receiving device 11, so as to drive a movement of the living organism 90 and control a moving direction thereof.

The liquid buffer circulating device 14 of the imaging system 10 is in communication with the receiving device 11 and is used to provide liquid 141. In one embodiment, the liquid 141 can be water or biological broth. Specifically, for example, the living organism 90 is a zebrafish and a zebrafish sperm, and the provided liquid 141 can be a liquid for a growing environment of the zebrafish or the zebrafish sperm. In another embodiment, the liquid 141 is filled in the receiving grooves 111 and the microchannel 112, such that the zebrafish and the zebrafish sperm can swim in the receiving grooves 111 and the microchannel 112. In a further embodiment, the liquid 141 located in the receiving device 11 can be replaced after a period of time. For example, the liquid providing device 14 can provide an unused liquid 141 into the receiving device 11 and can recycle the used liquid 141 located in the receiving device 11.

In some embodiments, the imaging system 10 can include a flow control device 16 electrically connected to the liquid buffer circulating device 14 and is used to adjust flow of the liquid 141. In a specific example, the flow rate can be determined according to the volume of the living organism 90 and the receiving device 11.

An image acquisition device 15 of the imaging system 10 neighbors a third side of the receiving device 11 and is used to capture an image of the living organism 90. In one embodiment, the image acquisition device 15 can be mounted above the receiving device 11 and capture the image downward. In a specific example, an image capturing area can be defined in the receiving device 11, and the living organism 90 is driven by the driving device 13 to move to the image capturing area, so as to capture the image. For example, the image capturing area is located at the microchannel 112. First, the living organism 90 can be driven by the driving device 13 to move to the microchannel 112. Then, the flipping angle φ of the microchannel 112 is changed by controlling the action of the magnetic cilia 113, so as to capture images of the living organism 90 at various angles.

In some embodiments, the imaging system 10 can include a controlling device 17 electrically connected to one of the magnetic field control device 12, the driving device 13, and the image acquisition device 15. In a specific example, the controlling device 17 is, for example, a computer, and an instruction can be outputted by the computer to control one of the magnetic field control device 12, the driving device 13, and the image acquisition device 15. In another embodiment, the controlling device 17 further includes a graphical user interface 171 configured to control one of the magnetic field control device 12, the driving device 13, and the image acquisition device 15 by inputting an instruction to the graphical user interface 171. For example, a magnetic field providing method of the magnetic field control device 12 is determined by the graphical user interface 171, so as to determine the action of the magnetic cilia 113. Or, the driving device 13 is controlled by the graphical user interface 171. For example, the light driving device 131 or the hydrodynamic device 132 is used to drive a movement of the living organism 90 and control a moving direction thereof, such that the living organism 90 achieves an area (such as moves to any one of the receiving device 111 or any one of the microchannel 112). Or, the image acquisition device 15 is controlled by the graphical user interface 171 to determine the timing of capturing the image.

In one embodiment, the imaging system con include a moving frame 18, wherein the receiving device 11 is disposed on the moving frame 18. One purpose of the moving frame 18 is to move the receiving device 11 by moving the moving frame 18, so as to change the position of the image acquisition apparatus 15 against the image capturing area of the receiving apparatus 11.

It is noted that the first side, the second side, and/or the third side described above are not particularly specified as any particular orientation of the receiving device 11. In the imaging system 10 according to one embodiment of the present disclosure, under the premise without affecting main functions of the components (for example, the receiving device 11, the magnetic field control device 12, the driving device 13, the liquid buffer circulating device 14, the image acquisition device 15, etc.), the magnetic field control device 12, the driving device 13, and the image acquisition device 15 can be disposed at any position neighboring the receiving device 11.

Several experimental data will be provided to prove that the imaging system 10 in one embodiment of the present disclosure has the effect described above.

Figure 3:
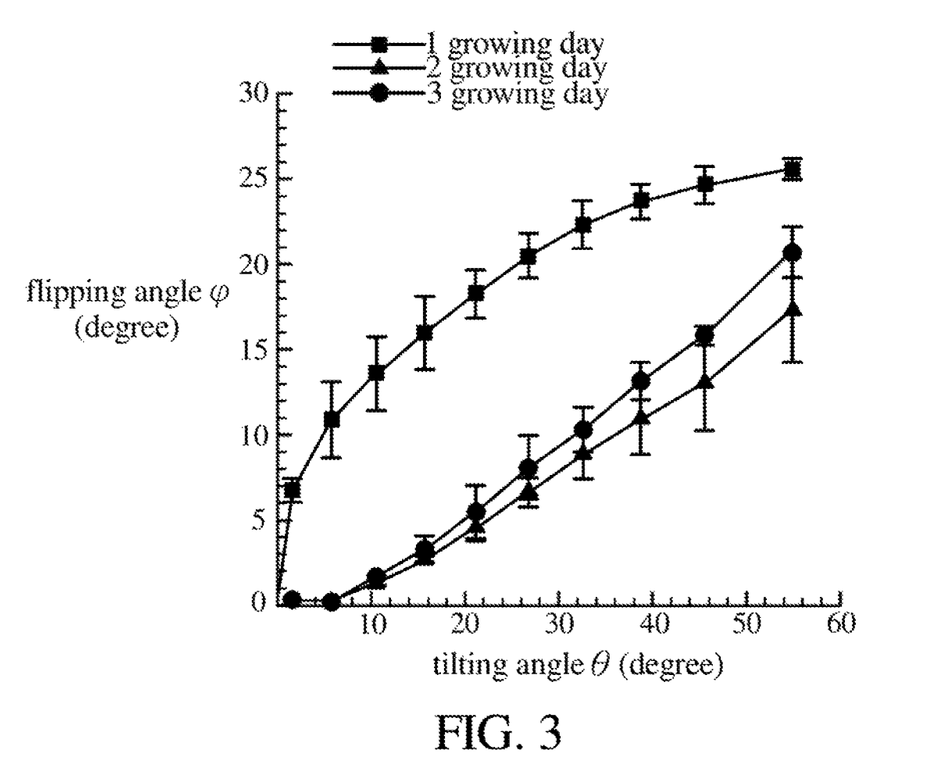
FIG. 3 is a schematic diagram illustrating relationship between tilting angles of the magnetic cilia and flipping angles of the zebrafish in different growing days.

Referring to FIG. 2C and FIG. 3, FIG. 2C is a cross-sectional diagram illustrating a tilting angle θ of the magnetic cilia 113 and a flipping angle φ of the living organism 90, and FIG. 3 is a schematic diagram illustrating relationship between tilting angles θ of the magnetic cilia 113 and flipping angles φ of the zebrafish on different growing days. As shown in FIG. 2C, the living organism 90 is, for example, a zebrafish. When the magnetic cilia 113 tilts leftward at a tilting angle θ along the axial direction 113A, the living animal 90 flips rightward at a flipping angle φ. In the experimental results as shown in FIG. 3, for the zebrafish on different growing days (such as 1 to 3 growing days), when the tilting angle θ is greater, the flipping angle φ is greater. In other words, the flipping angle φ of the zebrafish can be controlled by controlling the tilting angle θ of the magnetic cilia 113, so as to capture images of the living organism 90 at different angles. It is noted that for other growing days (for example, more than four growing days) of zebrafish, similar experimental results are also observed.

Next, the effect of activation of frozen zebrafish sperm can be achieved through the rotating action of the magnetic cilia 113. Referring to FIG. 2C and FIG. 2D, FIG. 2D is a three dimensional schematic diagram illustrating the magnetic cilia 113 with a rotating action. In this experiment, Embodiment 1 and Comparative Examples 1 to 3 are provided to compare with the activation of zebrafish sperm. In Embodiment 1, frozen zebrafish sperm are placed in the micro-channel 112, and the magnetic cilia 113 has a rotating action once per second (1 Hz) for about 5 seconds. Then, observation is performed whether zebrafish sperm are activated (e.g., beginning to move). In other Comparative Examples, frozen zebrafish sperm are placed in a liquid, and activation is respectively performed by the following methods, where Comparative Example 1 is at room temperature and no action is performed; Comparative Example 2 is at room temperature and a manual stirring is performed; and Comparative Example 3 is activated through a Vortex mixer at 3000 rpm. According to experimental results, the activating rate of Embodiment 1 is 63.8±4.2%, the activating rate of Comparative Example 1 is 14.1±7.6%, the activating rate of Comparative Example 2 is 43.9±4.1%, and the activating rate of Comparative Example 3 is 31.1±10.3%. From the above, the activating rate can be improved by the rotating action of the magnetic cilia 113.

Figure 4:
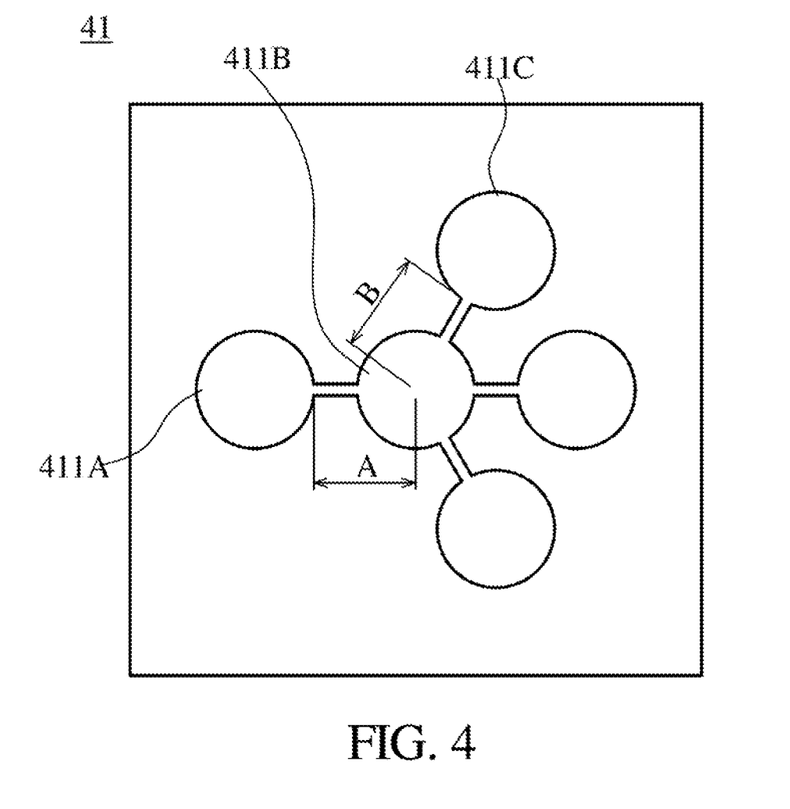
FIG. 4 is a schematic diagram illustrating a receiving device according to some embodiments of the present disclosure.

Next, the flow field changing device is used as the driving device to prove that a moving direction of the living organism can be driven. Referring to FIG. 1B and FIG. 4, FIG. 4 is a schematic diagram illustrating a receiving device 41 according to some embodiments of the present disclosure. In the present embodiment, the liquid 141 with a specific flow rate (e.g., 5 cm³/min) is inputted into a receiving groove 411A by the liquid buffer circulating device 14, and a recycling tube is connected with a receiving groove 411C to recycle the liquid 141 for producing a specific flow field. In the present embodiment, a zebrafish starts from the receiving groove 411A, passes through a receiving groove 411B, and reaches the receiving groove 411C, where diameters of the receiving groove 411A, 411B, and 411C are 10 mm, where length A means a distance (such as 10.95 mm) between an edge of the receiving groove 411A and a center of the receiving groove 411B, and where length B means a distance (such as 10.95 mm) between an edge of the receiving groove 411C and a center of the receiving groove 411B. In the present embodiment, the zebrafish substantially takes only about 4 to 10 seconds to start from the receiving groove 411A and reach the receiving groove 411C by the driving of the hydrodynamic driving device.

Next, the light driving device is used as the driving device to prove that a moving direction of the living organism can be driven. The light projecting device projects a dynamic pattern, and the linear bright fringes and the linear dark fringes of the dynamic pattern move along a proceeding direction, where the proceeding direction is vertical to an extending direction of the linear bright fringes (and/or the linear dark fringes).

Figure 5A:
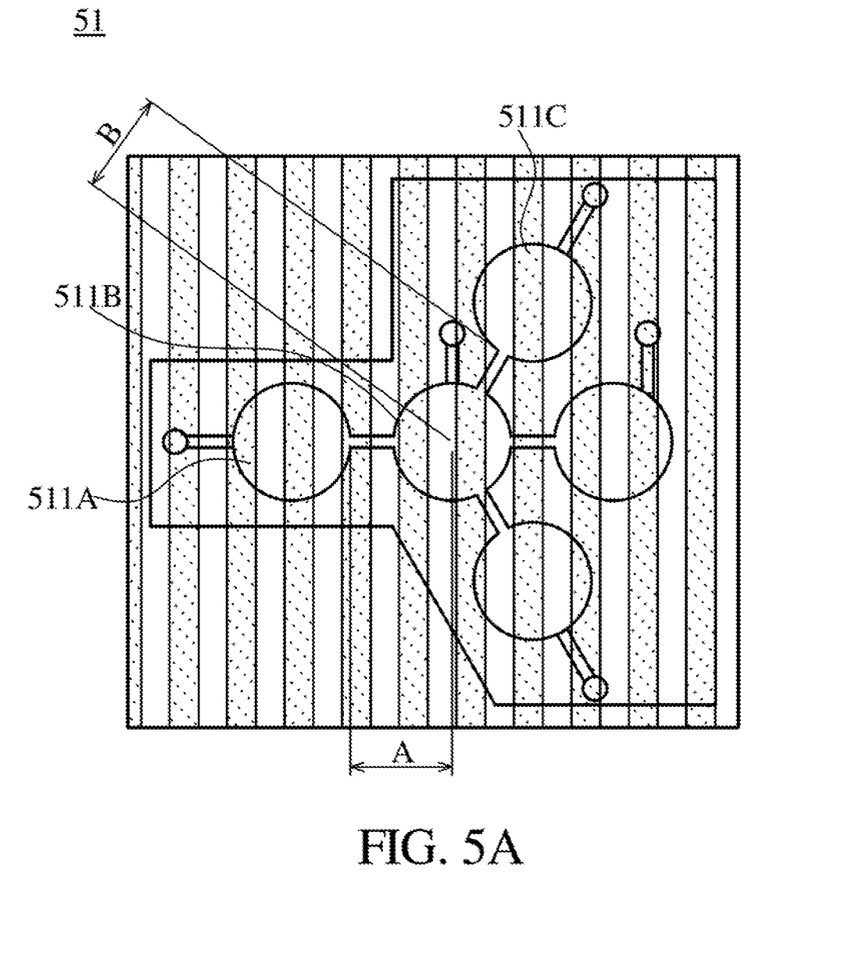
FIG. 5A and FIG. 5B are schematic diagrams illustrating a receiving device and a dynamic pattern according to some embodiments of the present disclosure.
Figure 5B:
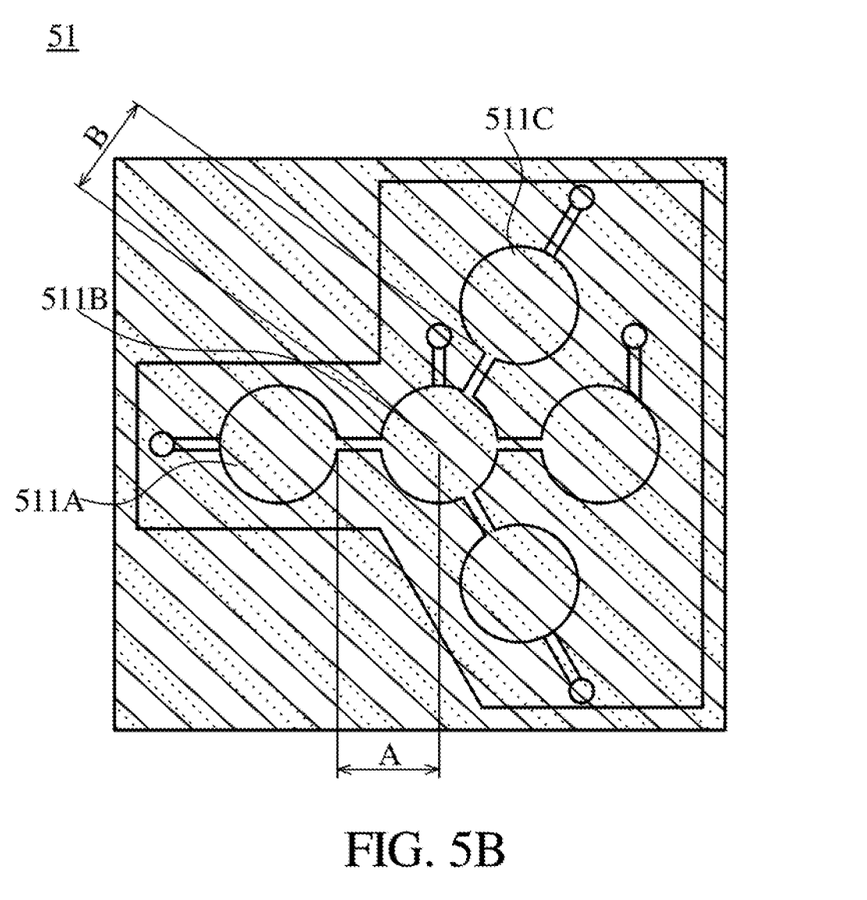

Next, referring to FIG. 1B, FIG. 5A, and FIG. 5B, FIG. 5A and FIG. 5B are schematic diagrams illustrating a receiving device 51 and a dynamic pattern according to some embodiments of the present disclosure. Similarly, in the present embodiment, a zebrafish starts from a receiving groove 511A, passes through a receiving groove 511B, and reaches a receiving groove 511C, where diameters of the receiving groove 511A, 511B, and 511C are 10 mm, where length A means a distance (such as 9.475 mm) between an edge of the receiving groove 511A and a center of the receiving groove 511B, and where length B means a distance (such as 8.625 mm) between an edge of the receiving groove 411C and a center of the receiving groove 511B. In the present embodiment, when the zebrafish starts from the receiving groove 511A, the linear bright fringes and the linear dark fringes as shown in FIG. 5A are projected by the light driving device, where the linear bright fringes and the linear dark fringes are shifted toward the right side in FIG. 5A so as to drive the zebrafish toward the receiving groove 511B. Then, when the zebrafish reaches the receiving groove 511B, the linear bright fringes and the linear dark fringes as shown in FIG. 5B are projected by the light driving device, where the linear bright fringes and the linear dark fringes are shifted toward the upper right side in FIG. 5B so as to drive the zebrafish toward the receiving groove 511C. According to the experimental results, the proceeding direction of the linear bright fringes and the linear dark fringes has a positive correlation with the moving direction of the living organism (such as the zebrafish of more than 3 growing days). According to a further experiment result, the use of full bright light (i.e., without dark fringes) does not produce such positive correlations. In summary, the imaging system suitable for the living organism of one embodiment of the present disclosure can drive the moving direction of the living organism by the light projecting device.

In addition, in the above experimental results using a light driving device as a driving device, different moving rates of dynamic patterns have different effects on the driving effect of zebrafish. For example, at a low moving rate (e.g., the frequency of appearance of the dynamic pattern is 0.5 Hz), the average time it takes for the zebrafish to move from the receiving groove 511A to receiving groove 511B is 5.4 seconds (which may also be referred to as the moving time of length A), and the average time it takes for the zebrafish to move from the receiving groove 511B to the receiving groove 511C is 19.6 seconds (which may also be referred to as the moving time of the length B). The relevant experimental data can refer to Table 1 below, in which it can be found that when the frequency of the appearance of the dynamic pattern is 1.5 Hz, the average time taken by the zebrafish is minimum.

TABLE 1

| Frequency of appearance of dynamic pattern | 0.5 Hz | 1 Hz | 1.5 Hz | 2 Hz |
| --- | --- | --- | --- | --- |
| Distance of length A | 9.475 mm | | | |
| Moving time of length A | 5.4 seconds | 3.7 seconds | 3.3 seconds | 5.3 seconds |
| Distance of length B | 8.625 mm | | | |
| Moving time of length B | 19.6 seconds | 9.3 seconds | 3.8 seconds | 21.51 seconds |

The present disclosure has been described with a preferred embodiment thereof and it is understood that many changes and modifications to the described embodiment can be carried out without departing from the scope and the spirit of the disclosure that is intended to be limited only by the appended claims.

The invention claimed is:

1. An imaging system, suitable for a living organism, comprising:
   a receiving device configured to receive the living organism, the receiving device comprising:
      at least one micro-channel; and
      a plurality of magnetic cilia disposed on a surface of the at least one micro-channel, wherein each of the magnetic cilia has an axial direction vertical to the surface of the at least one micro-channel, and the magnetic cilia comprises:
         a rotating action, wherein each of the magnetic cilia has a tilting angle with respect to the axial direction, and the magnetic cilia rotate around a rotation axis defined by the axial direction;
   a magnetic field controller neighboring a first side of the receiving device and providing a magnetic field to control the rotating action;

a light projector neighboring a second side of the receiving device, wherein the light projector projects a light pattern into the receiving device, and the light pattern comprises a plurality of linear bright fringes and a plurality of linear dark fringes, both of which are alternately arranged in sequence, wherein the light pattern is a dynamic pattern, and the linear bright fringes and the linear dark fringes move along a proceeding direction, wherein the proceeding direction of the linear bright fringes and the linear dark fringes has a positive correlation with a moving direction of the living organism, wherein frequency of an appearance of the dynamic pattern ranges from 1 Hz to 1.5 Hz;

a liquid buffer circulator in communication with the receiving device; and an image acquirer neighboring a third side of the receiving device.

2. The imaging system according to claim 1, wherein the living organism is one of a zebrafish and a zebrafish sperm.

3. The imaging system according to claim 1, further comprising a moving frame, wherein the receiving device is disposed on the moving frame.

4. The imaging system according to claim 1, further comprising a flow controller electrically connected to the liquid buffer circulator.

5. The imaging system according to claim 1, further comprising a controlling device electrically connected to one of the magnetic field controller, the light projector, and the image acquirer.

6. The imaging system according to claim 5, wherein the controlling device further comprises a graphical user interface configured to control one of the magnetic field controller, the light projector, and the image acquirer by inputting an instruction to the graphical user interface.

* * * * *